US005683431A

United States Patent [19]
Wang

[11] Patent Number: 5,683,431
[45] Date of Patent: Nov. 4, 1997

[54] VERIFICATION OF CAPTURE BY SENSING EVOKED RESPONSE ACROSS CARDIOVERSION ELECTRODES

[75] Inventor: Li Wang, White Bear Township, Minn.

[73] Assignee: Medtronic, Inc., Minneapolis, Minn.

[21] Appl. No.: 622,802

[22] Filed: Mar. 27, 1996

[51] Int. Cl.⁶ .................................................. A61N 1/362
[52] U.S. Cl. ........................................................ 607/28
[58] Field of Search ..................................... 607/28, 4, 11

[56] References Cited

U.S. PATENT DOCUMENTS

| | | |
|---|---|---|
| 4,727,877 | 3/1988 | Kallok . |
| 5,117,824 | 6/1992 | Keimel . |
| 5,165,404 | 11/1992 | Andersson . |
| 5,165,405 | 11/1992 | Eckwall . |
| 5,172,698 | 12/1992 | Stanko . |
| 5,285,780 | 2/1994 | Tsuji . |
| 5,312,441 | 5/1994 | Mader . |
| 5,324,310 | 6/1994 | Greeninger . |
| 5,331,966 | 7/1994 | Bennett . |
| 5,336,244 | 8/1994 | Weijand . |
| 5,342,406 | 8/1994 | Thompson . |
| 5,350,410 | 9/1994 | Kleks et al. ............................ 607/28 |

Primary Examiner—Scott M. Getzow
Attorney, Agent, or Firm—Reed A. Duthler; Harold R. Patton

[57] ABSTRACT

A threshold detection and capture verification system for a cardiac pacemaker/cardioverter/defibrillator (PCD) of the type comprising an implantable pulse generator (IPG) and a lead system including one or more pacing leads each having a proximal end coupled to the IPG and a distal end with at least one pace/sense electrode in contact with a patient's heart and one or more defibrillation leads having a proximal end coupled to the IPG and a distal end having one or more defibrillation electrodes in contact with a patient's heart or otherwise implanted within the patient's body. In a threshold detection operation, a sense amplifier is coupled to a selected threshold sensing electrode pair comprising at least one and preferably two defibrillation electrodes, and pacing pulses are applied to a pair of pace/sense electrodes. The evoked responses to pacing pulses having energy levels exceeding the stimulation threshold of the heart are detected through the sense amplifier and capture verified. The stimulation threshold is determined by incrementally reducing the pacing pulse energy until an evoked response is not sensed. The pacing pulse energy may then be adjusted to a level providing a safety margin above the stimulation threshold.

15 Claims, 5 Drawing Sheets

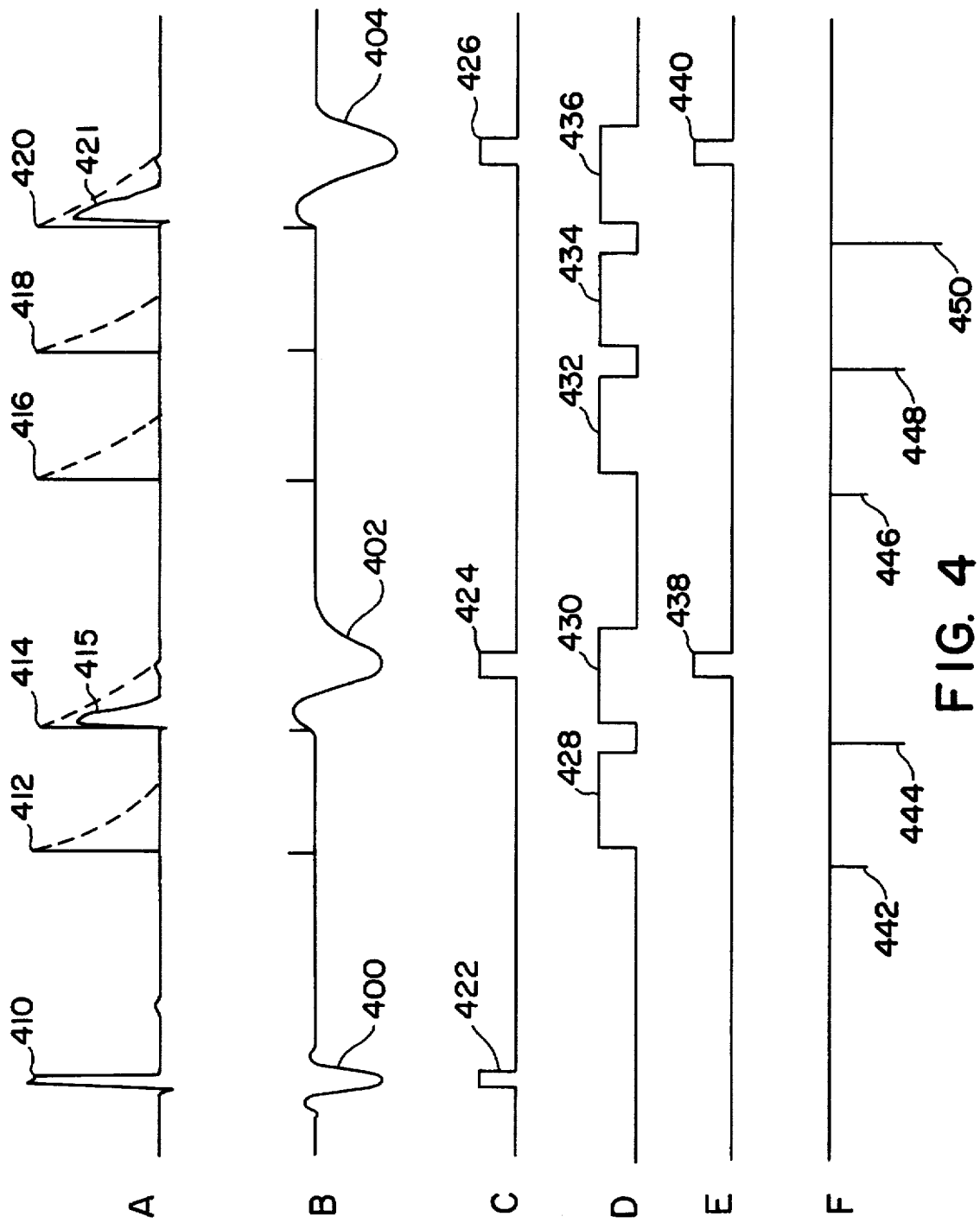

VERIFICATION OF CAPTURE BY SENSING EVOKED RESPONSE ACROSS CARDIOVERSION ELECTRODES

FIELD OF THE INVENTION

The present invention generally relates to implantable pacemaker/cardioverter defibrillators and more particularly to a method and apparatus for testing and detecting capture of the heart in response to a pacing pulse energy, deriving and storing stimulation threshold data, and adjusting pacing pulse energy for energy efficiency.

BACKGROUND OF THE INVENTION

By way of definition, in the field of automatic implantable arrhythmia control devices, e.g. implantable cardioverter/defibrillators (ICDs) and pacemaker/ cardioverter/ defibrillators (PCDs) the term "cardioversion" or "cardioverter" refers to the process of and device for discharging relatively high energy electrical shocks into or across cardiac tissue to arrest a life threatening tachyarrhythmia. The delivery of cardioversion shocks may or may not be synchronized with a cardiac depolarization or rhythm and may be applied to arrest a malignant ventricular tachycardia or ventricular fibrillation with a selectable or programmable shock energy. In practice, the arrest of atrial or ventricular tachycardia or fibrillation by such shocks delivered in synchrony with a cardiac depolarization is typically referred to as "cardioversion". Similarly, the arrest of atrial or ventricular fibrillation by a shock delivered without such synchronization is typically referred to as "defibrillation". In the following description and claims, it is to be assumed that these terms are interchangeable, and that use of one term is inclusive of the other device or operation, unless specific distinctions are drawn between them.

As described in commonly assigned U.S. Pat. No. 5,320, 643, incorporated herein by reference, a cardiac pacemaker implantable pulse generator (IPG) is an electrical device used to supplant some or all of an abnormal heart's natural pacing function by delivering appropriately timed electrical stimulation signals designed to cause the myocardium of the heart to contract or "beat", i.e. to "capture" the heart. Stimulation pulses provided by implanted pacemakers usually have well-defined amplitude and pulse width characteristics which can be adjusted by remote programming and telemetry equipment to meet physiologic and device power conservation needs of the particular patient.

In recent years, pacemakers have been incorporated in combination with cardioverters and defibrillators as pacemaker/cardioverter/defibrillators (PCD IPGs) of the type exemplified by the MEDTRONIC Model 7217 PCD device, for example, and successor models marketed by the assignee of the present invention. The Model 7217 PCD device provides programmable staged therapies including anti-tachycardia pacing regimens and cardioversion energy and defibrillation energy shock regimens in order to terminate a tachyarrhythmia with the most energy efficient and least traumatic therapies (if possible), as well as single chamber bradycardia pacing therapies. The Model 7217 PCD device provides a programmable energy, single polarity wave form, shock from the discharge of a high voltage output capacitor bank through a pair of electrodes disposed in relation to the heart. In addition, pacing pulse energy is also programmable for bradycardia and tachycardia treatments. Such a PCD device is disclosed, for example, in commonly assigned U.S. Pat. No. 5,312,441.

The strength (amplitude) and duration (pulse width) of the pacing pulses must be of such an energy magnitude above the stimulation threshold that capture is maintained to prevent serious complications and even death. Yet, it is desirable for these energy magnitudes not to be higher than the stimulation threshold than is needed for a reasonable "safety margin" in order to prolong battery life. The patient's stimulation thresholds in the atrium and ventricle often fluctuate in the short term, and gradually change in the long term. It has been clinically observed that the lowest stimulation threshold is observed immediately after implantation of the pacemaker (the acute threshold). Inflammation in the cardiac tissue around the tip of the pacing lead electrode drives the stimulation threshold up sharply during the first two to six weeks after implant to its highest level (the peak threshold), and greater pacing pulse energy is required to effect capture during this period. Some of the inflammation reduces over the long-term, to lower the threshold below the peak level—the chronic threshold. However, the chronic threshold does not reduce to the acute level, since some permanent fibrous tissue, requiring greater energy than non-fibrous tissue for signal propagation, remains around the electrode tip. In the short term, thresholds may decrease with exercise, for example, and may increase with various activities, including sleep. Consequently, the safety margin is typically set by the physician on implantation of the pacemaker to account for projected maximal stimulation thresholds.

As described in commonly assigned U.S. Pat. No. 5,324, 310, incorporated herein by reference, the post-operative determination of the stimulation thresholds by the physician typically requires the patient to be connected to surface ECG equipment while a threshold routine is conducted using the pacemaker programmer. The pacemaker programmer remotely effects the successive temporary reprogramming of the pulse width and/or amplitude to ascertain the points at which capture is lost, and a strength-duration curve may be plotted from the resulting threshold data. In this process, pacing pulses are delivered to either heart chamber at a test pacing rate above the patient's own underlying rate, and the pace pulse energy is decreased from pulse to pulse in a preset pattern. The pacing pulses are observed on a display or paper tracing as spikes, and capture or loss of capture (LOC) is observed by the presence or absence of the evoked cardiac response waveshape (a P-wave or an R-wave) that follows each spike. At LOC, the pacing pulse energy may be immediately restored so that the patient does not experience syncope. The resulting threshold data may be used to permanently reprogram the pulse energy. Naturally, such periodic patient studies are time consuming and expensive to conduct. Moreover, they do not provide an indication of stimulation threshold fluctuation over the course of a patient's day and levels of activity. The life of the IPG is shortened as the battery is depleted at a rate higher than necessary to meet the patient's needs.

As a result of these considerations, a great deal of effort has been expended over many years to develop pacemaker IPGs having the capability of automatically testing the stimulation threshold, i.e. providing an "auto-capture" detection function, and resetting the pacing pulse energy to exceed the threshold by the safety margin without the need for clinical or patient intervention. A wide variety of approaches have been taken as reflected by the extensive listing of earlier patents described in the commonly assigned '310 and '643 patents and in further U.S. Pat. Nos. 5,165, 404, 5,165,405, 5,172,690, 5,222,493, 5,285,780, and 5,331, 966.

In such pacemaker IPGs, the capture detection approaches have taken a variety of forms typically in the attempt to overcome the difficulty in detecting the evoked cardiac response wave shape from the pacing electrodes employed to deliver the pacing pulse. The high stimulation energy pacing pulse and the ensuing after-potentials and electrode-tissue polarization artifacts mask the evoked response, and also saturate the sense amplifiers coupled to the electrodes, until they dissipate. By the time that the sense amplifier is no longer blinded, the evoked response, if any, has typically passed the electrodes. Many of the approaches that have been taken include blanking intervals for the sense amplifiers combined with efforts to suppress or attenuate or compensate electronically for the composite post-delivery signal levels at the sense amplifier input during the blanking intervals to shorten the saturation period (and the blanking interval) as much as possible.

Alternatively, the use of separate "far field" EGM amplifiers and electrode systems from those "near field" electrode systems used in delivering the pacing pulse have been proposed in a variety of configurations, as exemplified by the above referenced '310 patent. Additional far-field electrodes and sense amplifiers are proposed in the above-referenced '966 and '493 patents. The function and accuracy of the these approaches for determining LOC have been adversely affected by one or more of factors including, but not limited to myopotentials (electrical signals which are the product of muscle movement) and stray electromagnetic interference (EMI).

The above-described prior an approaches are applied to pacemaker IPGs. A need exists for a simple system for detecting capture and LOC from evoked P-waves and/or R-waves in PCD IPGs for use in determining the pacing energy threshold in one or both of the heart chambers and automatically adjusting the delivered pacing pulse energy for that chamber.

SUMMARY OF THE INVENTION

Accordingly, it is an object of the present invention to provide a practical and durable system in a PCD IPG and associated lead system for sensing the evoked response to a pacing pulse for determining the capture/LOC stimulation threshold in one or both chambers of the heart.

It is a further object of the present invention to provide a PCD IPG having a capture detection feature without requiring any significant additional special leads or electrodes, indwelling sensors or sophisticated processing of the evoked response signals.

These and other objects of the invention are realized in a system implemented in a PCD IPG for determining a stimulation threshold of a heart chamber following delivery of a pacing pulse comprising: a defibrillation lead system having at least one defibrillation electrode positioned in relation to a patient's heart; a pacing lead system having at least one pacing electrode positioned in relation to a patient's heart and a further pacing electrode; sense amplifier means for sensing electrical depolarizations of the heart and providing a sense detect signal in response thereto; means operable in a threshold test mode for coupling a threshold sensing electrode pair comprising at least the defibrillation electrode to the sense amplifier means; pacing pulse generator means operable in the threshold test mode for delivering at least one pacing pulse at a stimulation threshold test energy level to the patient's heart through the pacing lead system; and means responsive to a sense detect signal of the sense amplifier means for determining capture of the patient's heart by a pacing pulse delivered at the stimulation threshold test energy level.

In accordance with the invention, a method and apparatus for determining capture of the heart following delivery of a pacing pulse comprises the steps of and means for: in a threshold determination operation, coupling at least one defibrillation electrodes to the sense amplifier means; in the threshold determination operation, delivering at least one pacing pulse at a stimulation threshold test energy level to the patient's heart through the pacing electrodes; sensing electrical depolarizations of the heart by the sense amplifier means in response to the delivered pacing pulse and providing a sense output signal in response; and determining capture of the patient's heart by a pacing pulse delivered at the stimulation threshold test energy level in response to a sense output signal.

The method and apparatus also preferably comprises the steps of and means for: detecting the absence of a sense output signal in response to a delivered pacing pulse; and determining loss of capture of the patient's heart by a pacing pulse delivered at the stimulation threshold test energy level in response to the detected absence of a sense output signal.

Preferably, the defibrillation lead system comprises at least two defibriilation electrodes positioned with respect to the heart chamber, and the inputs of sense amplifier are coupled to the two defibrillation electrodes in the threshold test mode for sensing the evoked response depolarization wave. Alternatively, in a dual chamber PCD system, one input of the sense amplifier may be coupled to a pace/sense electrode that is not used to deliver the pacing pulse. The selected electrodes coupled to the sense amplifier are referred to as "threshold sensing electrodes" or "threshold sensing electrode pairs".

Preferably, a switch matrix is operated in the threshold determination operation to couple the defibriilation electrode(s) to the input terminals of a sense amplifier normally coupled to a pacing lead. In a dual chamber PCD system, either the atrial or ventricular sense amplifier may be employed. In an alternative embodiment, the switch matrix is operated in the threshold determination operation to couple the defibrillation electrode(s) to the input terminals of a sense amplifier normally used for sensing the electrogram (EGM) for data storage.

The present invention may be implemented in single and dual chamber PCD systems employing any of the combinations of pacing and defibrillation leads that are presently employed or that have been proposed.

The present invention provides the PCD IPG with the ability to detect capture, LOC and determine the pacing energy thresholds in the atrium and/or the ventricle without adding additional leads, electrodes, connector block elements, sensors or other structure to the PCD IPG. In one preferred embodiment, only an additional switching network is required between the sense amplifiers and the pace/sense and defibrillation thresholds operable under the control of the IPG microcomputer to perform threshold testing and determination at selected times. In a further preferred embodiment, further processing of the output signal of the EGM amplifier may be selectively enabled for sensing the evoked response depolarization wave.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein:

FIG. 4 is a timing diagram of the operation of the embodiment of FIGS. 1 and 2 which reflects the capture/LOC threshold detection function in a threshold detection mode;

DETAILED DESCRIPTION OF THE PREFERRED EMBODIMENTS

The preferred embodiments of the invention are preferably implemented in the context of an implantable PCD having single or dual chamber pacing and/or cardioverion/defibrillation capabilities of the types described in detail in the above-referenced '441 patent and in commonly assigned, U.S. patent application Ser. No. 08/293,769 filed Aug. 19, 1994, for ATRIAL DEFIBRILLATOR AND METHOD OF USE, respectively, incorporated herein by reference in their entireties. Such PCDs may be constructed or made programmable to provide atrial only, ventricular only, or both atrial and ventricular pacing modes. The pacing modes also preferably include either or both bradycardia compensating pacing modes or anti-tachycardia pacing therapies. In addition, the present invention may be employed with a wide variety of defibrillation electrode combinations.

Figure 1:
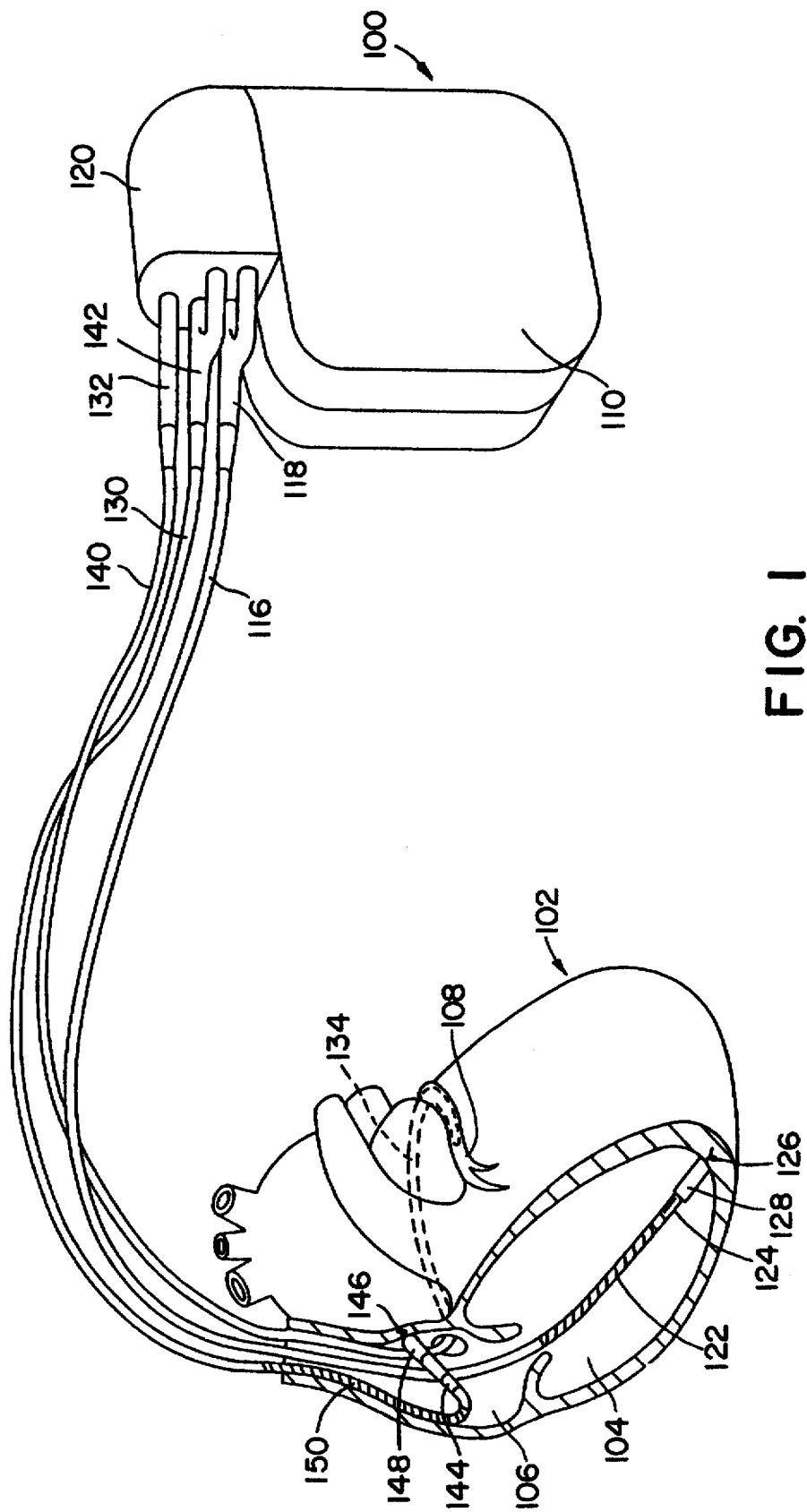
FIG. 1 is a schematic illustration of an atrial and venticular chamber pacemaker/cardioverter/defibrillator IPG implanted in a patient's chest with an IPG can electrode and endocardial leads transvenously introduced into the RA, CS and RV of the heart wherein capture of atrial and/or ventricular pacing pulses may be detected across selected threshold sensing electrode pairs.
Figure 2:
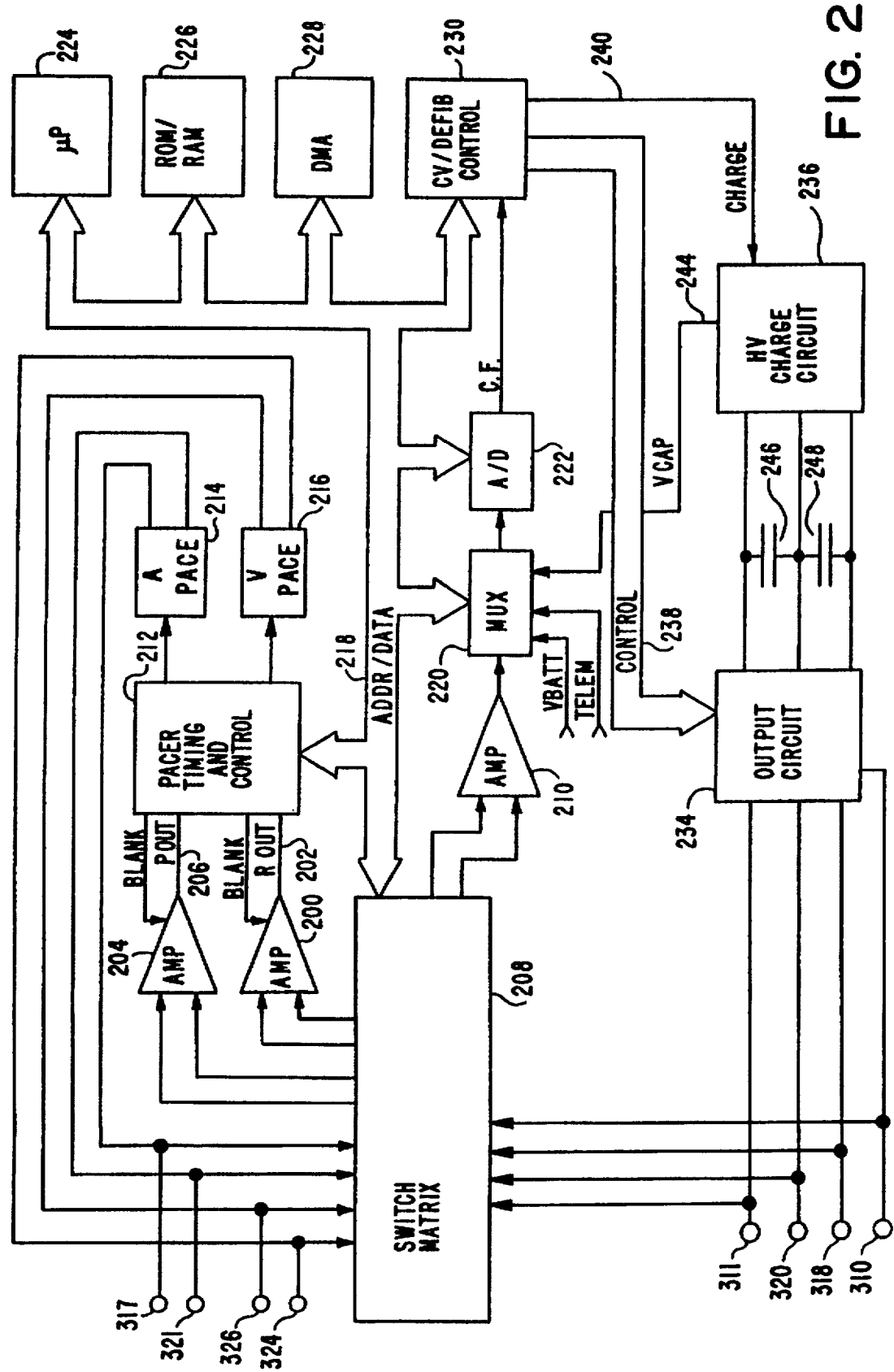
FIG. 2 is a block diagram of the IPG of FIG. 1 in which the present invention may be practiced by sensing the evoked response to a pacing pulse across a selected threshold sensing electrode pair.

FIGS. 1 and 2 illustrate a dual chamber, multi-programmable, PCD IPG and associated lead system for providing atrial and/or ventricular sensing functions for detecting P-waves of atrial depolarizations and/or R-waves of ventricular depolarizations, depending on the programmed pacing and/or sensing mode and delivering pacing or cardioversion/defibrillation therapies. An exemplary defibrillation lead system is depicted in FIG. 1 for delivering cardioversion/defibrillation shock therapies to the atria or ventricles of the heart. FIGS. 1 and 2 are intended to provide a comprehensive illustration of each of the atrial and/or ventricular, pacing and/or cardioversion/defibrillation configurations that may be effected using sub-combinations of the components depicted therein and equivalents thereto.

In the preferred embodiment of FIGS. 1 and 2, depending on the programmed pacing mode, pacing pulses may be applied to the atrium and/or ventricle in response to the detection of the appropriate bradycardia condition by the PCD IPG 100. The pacing and sensing functions are effected through atrial and ventricular bipolar pace/sense electrode pairs at the ends of right atrial/superior vena cava (RA/SVC) and right ventricular (RV) leads 140 and 116, respectively, fixed in the right atrium 106 and right ventricle 104, respectively, that are electrically coupled to the circuitry of IPG 100 through a connector block 120. Delivery of cardioversion or defibrillation shocks to the atrial and/or ventricular chambers of the heart 102 may be effected through selected combinations of the illustrated exemplary RA and RV defibrillation electrodes on the RA/SVC and RV leads and an additional coronary sinus (CS) electrode on a CS lead 130 as well as an exposed surface electrode 110 of the outer housing or can of the IPG 100. The can electrode 110 optionally serves as a subcutaneous defibrillation electrode, used as one electrode optionally in combination with one inncardiac defibrillation electrode for cardioverting or defibrillating either the atria or ventricles. A remote, subcutaneous defibrillation patch electrode may be provided in addition to or substitution for the can electrode 110.

The RV lead 116 is depicted in a conventional configuration and includes an elongated insulating lead body, enclosing three concentric, electrically isolated, coiled wire conductors, separated from one another by tubular insulating sheaths. Located adjacent the distal end of the RV lead 116 are a pace/sense ring electrode 124, a helical, pace/sense electrode 126, mounted retractably within an insulating electrode head 128. Helical electrode 126 is adapted to be extended out of the electrode head 128 and screwed into the ventricular apex in a manner well known in the art. RV pace/sense electrodes 124 and 126 are each coupled to a coiled wire conductor within the RA lead body and are employed for cardiac pacing in the ventricle and for sensing near-field R-waves. RV lead 116 also supports an elongated, exposed wire coil, defibrillation electrode 122 in a distal segment thereof adapted to be placed in the right ventricle 104 of heart 102. The RV defibrillation electrode 122 may be fabricated from platinum, platinum alloy or other materials known to be usable in implantable defibrillation electrodes and may be about 5 cm in length. Defibrillation electrode 122 is also coupled to one of the coiled wire conductors within the lead body of RV lead 116. At the proximal end of the lead body is a bifurcated connector end 118 having three exposed electrical connectors, each coupled to one of the coiled conductors, that are attached within the connector block 120 to connector block terminals in a manner well known in the art.

The coronary sinus (CS) lead 130 includes an elongated insulating lead body enclosing one elongated coiled wire conductor coupled to an elongated exposed coil wire defibrillation electrode 134. CS defibrillation electrode 134, illustrated in broken outline, is located within the coronary sinus and great vein 108 of the heart 102 and may be about 5 cm in length. At the proximal end of the CS lead 130 is a connector end 132 having an exposed connector coupled to the coiled wire conductor and attached within the connector block 120 to connector block terminals in a manner well known in the art.

The RA/SVC lead 140 includes an elongated insulating lead body carrying three concentric, electrically isolated, coiled wire conductors separated from one another by tubular insulating sheaths, corresponding generally to the structure of the RV lead 116. The lead body is formed in a manner well known in the art in an atrial J-shape in order to position its distal end in the right atrial appendage. A pace/sense ring electrode 144 and an extendable helical, pace/sense electrode 146, mounted retractably within an insulating electrode head 148, are formed distally to the bend of the J-shape. Helical electrode 146 is adapted to be extended out of the electrode head 148 and screwed into the atrial appendage in a manner well known in the art. RA pace/sense electrodes 144 and 146 are employed for atrial pacing and for near-field sensing of P-waves. An elongated, exposed coil defibrillation RA/SVC electrode 150 is supported on RA lead 140 extending proximally to pace/sense ring electrode 144 and coupled to the third coiled wire conductor within the RA lead body. Electrode 150 preferably is 10 cm in length or greater and is configured to extend from within the SVC and toward the tricuspid valve. At the proximal end of the RA lead 140 is a bifurcated connector 142 which carries three exposed electrical connectors, each coupled to one of the coiled wire conductors, that are attached within the connector block 120 to connector block terminals in a manner well known in the art.

Preferably, bipolar pace/sense electrodes are employed in the practice of the invention, but their configuration, fixation in contact with, and positioning with respect to the atria and ventricles may differ from those shown in FIG. 1. Unipolar pace/sense electrode bearing leads may also be used in the practice of the invention, and the second, return electrode may be one or more of the defibriilation electrodes.

In accordance with the present invention, the circuitry of FIG. 2 within PCD IPG 100 communicates with an external programmer (not shown) through an RF communication link in a manner well known in the art. The pacing pulse energy threshold for capturing the atrium and/or the ventricle of heart 102 with pacing pulses delivered across the atrial pace/sense electrodes 144, 146 and/or the ventricular pace/sense electrodes 124, 126 may be tested in a threshold determination operation initiated by commands from the external programmer. In addition, in accordance with the present invention, the circuitry itself may be programmed to initiate a capture detection sequence automatically on a periodic basis, e.g. when the patient is expected to be sleeping, to test for the capture/LOC stimulation threshold and to reset the stimulation pulse energy to a safety margin above the pacing pulse stimulation threshold. In either case, it is necessary to detect the evoked response, i.e., the stimulated P-wave and/or R-wave during the time that polarization after-potentials appear on the pace/sense electrodes as a result of the preceding test pacing pulse.

The PCD system configuration and operating modes of FIG. 1 may be varied by eliminating: (1) the atrial or ventricular pacing capability including the associated pace/sense electrodes thereby providing dual chamber cardioversion/defibrillation and single chamber bradycardia/tachycardia pacing capabilities; (2) in a single chamber PCD, the atrial or ventricular pacing and sensing capability along with the corresponding chamber cardioversion/defibrillation capability and associated leads and electrodes; (3) the atrial or ventricular cardioversion/defibrillation capability and associated lead and electrodes while retaining the dual chamber pacing and sensing capability thereby providing single chamber cardioversion/defibrillation and dual chamber bradycardia/tachycardia pacing capabilities; or (4) in a special case of an atrial PCD, the ventricular cardioversion/defibrillation capability while retaining at least the atrial pace/sense capability and the ventricular sense capability for providing R-wave synchronization of the delivered atrial cardioversion therapies. In each such system, it will be understood that appropriate defibrillation and pacing leads will be employed in the system.

In accordance with the present invention, the detection of the evoked response, is facilitated by using same chamber threshold sensing electrode pair including at least one defibrillation electrode, if present, or an available threshold sensing electrode pair, including at least one defibrillation electrode, closest to the chamber being paced. For example, in FIG. 1, in one preferred atrial threshold testing routine, the test energy pacing pulses are delivered across the atrial pace/sense electrodes 144 and 146. The atrial sense amplifier, for example, is coupled temporarily through a switch network via lead wire conductors of the RA/SVC and CS defibrillation electrodes 150 and 134, respectively. Similarly, in one preferred ventricular threshold test regimen, the test energy pacing pulses are delivered across the ventricular pace/sense electrodes 124 and 126. The ventricular sense amplifier, for example, is coupled temporarily through a switch network via lead wire conductors of the RV defibrillation electrode 122 and either the CS or the RA/SVC defibrillation electrodes 134 or 150, respectively. Sensing of an evoked P-wave or R-wave is facilitated because of the large surface area of electrodes 134, 150 or 122, 134/150 and the absence of any significant polarization after-potentials on these electrodes. Moreover, the sensing is relatively near-field, and myopotentials and other noise sources emanating from outside the heart have less effect on sensing, than is the case with far-field electrodes.

In a simpler PCD system employing the IPG can electrode 110 in conjunction with only one other defibrillation electrode located in proximity to the atrium or ventricle, e.g. electrodes 122 or 150, then it is desirable to couple the appropriate sense amplifier input terminals to the available defibrillation electrodes. Alternatively, an inactive pace/sense electrode may be substituted for the can electrode 110. The same substitutions may be made for the case where one of the defibrillation electrodes is a defibrillation electrode implanted subcutaneously and more remote from the heart chamber.

FIG. 2 is a functional schematic diagram of the circuitry of a dual chamber, implantable pacemaker/cardioverter/defibrillation 100 in which the present invention may usefully be practiced. Certain of the pace/sense and cardioversion/ defibrillation functions may be disabled or not provided to configure the PCD device to operate in other dual chamber or single chamber PCD operating modes including the above-described modes (1)–(4). Therefore, FIG. 2 should be taken as exemplary of the circuitry of the type of single chamber or dual chamber PCD IPG 100 in which the invention may be embodied, and not as limiting, as it is believed that the invention may usefully be practiced in a wide variety of device implementations, as long as a pacing mode providing either bradycardia pacing or tachycardia pacing therapies is retained.

The PCD IPG circuitry of FIG. 2 includes a high voltage section for providing relatively high voltage cardioversion/defibrillation shocks when needed in response to detection of a tachyarrhythmia, a low voltage pace/sense section for sensing P-waves and/or R-waves and providing relatively low voltage bradycardia pacing and anti-tachycardia pacing therapies, both operated under the control of a microcomputer including a microprocessor 224, ROM/RAM 226 and DMA 228. Other functions, including uplink and downlink telemetry with an external programmer for interrogating or programming operating modes and parameters, are also provided in a manner well known in the art.

The block diagram of FIG. 2 depicts the atrial and ventricular pace/sense and defibrillation lead connector terminals of the connector block 120. Assuming the electrode configuration of FIG. 1, the correspondence to the illustrated leads and electrodes is as follows: Optional terminal 310 is hard wired to electrode 110, that is, the un-insulated portion of the housing of the PCD IPG 100, and technically may be directly connected and not be part of the connector block 120. Terminal 320 is adapted to be coupled through RV lead 116 to RV cardioversion/defibrillation electrode 122. Terminal 311 is adapted to be coupled through RA lead 140 to RA/SVC electrode 150. Terminal 318 is adapted to be coupled through CS lead 130 to CS defibrillation electrode 134. However, it will be understood that fewer terminals may be provided than depicted, and/or that one or more differing defibrillation leads, e.g. epicardial patch electrode and subcutaneous patch electrode bearing leads may also be employed for one or more of the depicted defibrillation electrode bearing leads.

Terminals 310, 311, 318 and 320 are coupled to high voltage output circuit 234. High voltage output circuit 234 includes high voltage switches controlled by CV/DEFIB CONTROL logic 230 via control bus 238. The switches within circuit 234 control which electrodes are employed and which are coupled to the positive and negative terminals of the capacitor bank including capacitors 246 and 248 during delivery of the intermediate and high voltage cardioversion and defibrillation shocks.

Terminals 324 and 326 of the connector block are adapted to be coupled through RV lead 116 to RV pace/sense electrodes 124 and 126 for sensing and pacing in the ventricle. Terminals 317 and 321 are adapted to be coupled through RA/SVC lead 140 to RA pace/sense electrodes 144 and 146 for sensing and pacing in the atrium. Terminals 324 and 326 are coupled to the inputs of R-wave sense amplifier 200 through switches in switch network 208. R-wave sense amplifier 200 which preferably takes the form of an automatic gain controlled amplifier providing an adjustable sensing threshold as a function of the measured R-wave signal amplitude. A VSENSE signal is generated on R-OUT line 202 whenever the signal sensed between electrodes 124 and 126 exceeds the current ventricular sensing threshold. Terminals 317 and 321 are coupled to the P-wave sense amplifier 204 through switches in switch network 208. P-wave sense amplifier 204 preferably also takes the form of an automatic gain controlled amplifier providing an adjustable sensing threshold as a function of the measured P-wave amplitude. An ASENSE signal is generated on P-OUT line 206 whenever the signal sensed between pace/sense electrodes coupled to terminals 317, 321 exceeds the current atrial sensing threshold. The A-PACE and V-PACE output circuits 214 and 216 are also coupled to terminals 317, 321 and 324, 326, respectively. The atrial and ventricular sense amplifiers 204 and 200 are isolated from the A-PACE and V-PACE output circuits 214 and 216 by appropriate isolation switches within switch matrix 208 and also by blanking circuitry operated by A-BLANK and V-BLANK signals during and for a short time following delivery of a pacing pulse in a manner well known in the art. The general operation of the R-wave and P-wave sense amplifiers 200 and 204 may correspond to that disclosed in U.S. Pat. No. 5, 117,824, incorporated herein by reference in its entirety.

Switch matrix 208 is also used in an EGM sensing mode to select which of the available pace/sense electrodes (or defibrillation electrodes) are coupled to the inputs of wide band (0.5–200 Hz) EGM sense amplifier 210 for use in digital signal storage and analysis of the patient's atrial and ventricular EGM. Therefore, the terminals 317, 321, adapted to be coupled to the atrial pace/sense electrodes 144, 146, and the terminals 324, 326, adapted to be coupled to the ventricular pace/sense electrodes 124, 126, are also coupled to the switch matrix 208. Switches within switch matrix 208 are selectively controlled by the microprocessor 224 or circuits within the pacer timing and control circuitry 212, via data/address bus 218, to couple the terminals 317, 321 or 324, 326 to the inputs of bandpass amplifier 210 and to thereby apply atrial or ventricular signals to the bandpass amplifier 210. Output signals from bandpass amplifier 210, in response to the applied atrial or ventricular signals, are provided to multiplexer 220, and thereafter converted to multi-bit digital signals by A/D converter 222, for storage in RAM in ROM/RAM 226 under control of DMA 228. Microprocessor 224 may employ digital signal and morphology analysis techniques to characterize the digitized signals stored in ROM/RAM 226 to recognize and classify the patient's heart rhythm employing any of the numerous signal processing methodologies known to the art.

The PCD IPG circuitry of FIG. 2 provides atrial and/or ventricular cardiac pacing for bradycardia and tachycardia conditions and synchronized cardioversion and defibrillation shock therapies for tachyarrhythmias in accordance with therapy regimes programmed by the physician. With respect to the pacing operations, the pacer timing and control circuitry 212 includes programmable digital counters which control the basic time intervals associated with bradycardia pacing modes including DDD, VVI, DVI, VDD, AAI, DDI and other modes of single and dual chamber pacing well known to the art. Pacer timing and control circuitry 212 also controls escape intervals associated with timing and delivering anti-tachyarrhythmia pacing in both the atrium and the ventricle, employing any anti-tachyarrhythmia pacing therapies known to the art. In the process, pacer timing and control circuitry 212 also times the operation of and processes ASENSE and VSENSE events on the P-OUT and R-OUT lines of the atrial and ventricular sense amplifiers 204 and 200. In the context of the present invention, pacer timing and control circuitry 212 responds to commands from microprocessor 224 to initiate a threshold determination operation and controls the switch matrix 208 to select the appropriate threshold sensing electrode pair, controls the use and operation of EGM amplifier 210 or the atrial and/or ventricular sense amplifiers 204, 200 in the threshold detection operation, and processes the sensed events all as described below.

In normal pacing modes of operation, intervals defined by pacer timing and control circuitry 212 include atrial and ventricular pacing escape intervals, blanking intervals, the refractory periods during which sensed P-waves and R-waves are ineffective to restart timing of the escape intervals, and the pulse widths of the pacing pulses. These intervals are determined by microprocessor 224, in response to stored data in RAM in ROM/RAM 226 and are communicated to the pacer timing and control circuitry 212 via address/data bus 218. Pacer timing and control circuitry 212 also determines the amplitude of the cardiac pacing pulses under control of microprocessor 224.

During pacing, the escape interval counters within pacer timing and control circuitry 212 are reset upon sensing of R-waves and P-waves as indicated by a signals on lines 202 and 206. In accordance with the selected pacing mode, pacer timing and control circuitry 212 provides pace trigger signals to the A-PACE and V-PACE output circuits 214 and 216 on timeout of the appropriate escape interval counters to trigger generation of atrial and/or ventricular pacing pulses. The pacing escape interval counters are also reset on generation of pacing pulses, and thereby control the basic timing of cardiac pacing functions.

With respect to anti-tachyarrhythmia pacing, the value of the counts present in the escape interval counters when reset by sensed R-waves and P-waves may be used as measures of the durations of R-R intervals, P-P intervals, P-R intervals and R-P intervals, which measurements are stored in RAM in ROM/RAM 226 and used to detect the presence of tachyarrhythmias as described below.

Microprocessor 224 operates as an interrupt driven device, and is responsive to interrupts from pacer timing and control circuitry 212 corresponding to the occurrence sensed P-waves (ASENSE) and R-waves (VSENSE) and corresponding to the generation of cardiac pacing pulses. These interrupts are provided via data/address bus 218. Any necessary mathematical calculations to be performed by microprocessor 224 and any updating of the values or intervals controlled by pacer timing/control circuitry 212 take place following such interrupts.

For example, in response to a sensed or paced ventricular depolarization or R-wave, the intervals separating that R-wave from the immediately preceding R-wave, paced or sensed (R-R interval) and the interval separating the paced or sensed R-wave from the preceding atrial depolarization, paced or sensed (P-R interval) may be stored. Similarly, in response to the occurrence of a sensed or paced atrial depolarization (P-wave), the intervals separating the sensed P-wave from the immediately preceding paced of sensed atrial contraction (P-P Interval) and the interval separating the sensed P-wave from the immediately preceding sensed or paced ventricular depolarization (R-P interval) may be stored. Preferably, a portion of RAM in the ROM/RAM 226 (FIG. 2) is configured as a plurality of recirculating buffers, capable of holding a preceding series of measured intervals, which may be analyzed in response to the occurrence of a pace or sense interrupt to determine whether the patient's heart is presently exhibiting atrial or ventricular tachyarrhythmia.

Detection of atrial or ventricular tachyarrhythmias, as employed in the present invention, may correspond to tachyarrhythmia detection algorithms known to the art. For example, presence of atrial or ventricular tachyarrhythmia may be confirmed by means of detection of a sustained series of short R-R or P-P intervals of an average rate indicative of tachyarrhythmia or an unbroken series of short R-R or P-P intervals. The suddenness of onset of the detected high rates, the stability of the high rates, or a number of other factors known to the art may also be measured at this time. In the event that an atrial or ventricular tachyarrhythmia is detected, and an anti-tachyarrhythmia pacing regimen is prescribed, appropriate timing intervals for controlling generation of anti-tachyarrhythmia pacing therapies are loaded from microprocessor 224 into the pacer timing and control circuitry 212, to control the operation of the escape interval counters therein and to defmerefractory periods during which detection of R-waves and P-waves is ineffective to restart the escape interval counters.

In the event that generation of a cardioversion or defibrillation shock is required, microprocessor 224 employs the an escape interval counter to control timing of such cardioversion and defibrillation pulses, as well as associated refractory periods. In response to the detection of atrial or ventricular fibrillation or tachyarrhythmia requiting a cardioversion pulse, microprocessor 224 activates cardioversion/defibrillation control circuitry 230, which initiates charging of the high voltage capacitors 246 and 248 via charging circuit 236, under control of high voltage charging control line 240. The voltage on the high voltage capacitors is monitored via VCAP line 244, and the monitored voltage signal is passed through multiplexer 220, digitized, and compared to a predetermined value set by microprocessor 224 in ADC/comparator 222. When the voltage comparison is satisfied, a logic signal on Cap Full (CF) line 254 is applied to cardioversion/defibrillation control circuti 230, terminating charging. Thereafter, timing of the delivery of the defibrillation or cardioversion shock is controlled by pacer timing/control circuitry 212. Following delivery of the fibrillation or tachycardia therapy, the microprocessor 224 then returns the operating mode to cardiac pacing and awaits the next successive interrupt due to pacing or the occurrence of a sensed atrial or ventricular depolarization.

In the illustrated device, delivery of the cardioversion or defibrillation pulses is accomplished by output circuit 234, under control of control circuitry 230 via control bus 238. Output circuit 234 determines whether a monophasic or biphasic pulse is delivered, the polarity of the electrodes and which electrodes are involved in delivery of the pulse. Output circuit 234 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in U.S. Pat. No. 4,727,877, incorporated by reference in its entirety.

In the event that, as in FIGS. 1 and 2, both atrial and ventricular defibrillation are available, ventricular defibrillation may be accomplished using higher pulse energy levels than required for atrial defibrillation and may employ the same or a different electrode set. For example, terminals 310, 311, 318 and 320 or only terminals 311, 318 and 320 may be employed for atrial defibrillation. Terminals 311, 320 and 310 might be employed for ventricular defibrillation, with terminal 311 (coupled to RA/SVC electrode 150) coupled to terminal 310 (can electrode 110). Alternatively, terminals 310, 318 and 320 may be employed, with terminal 318 (coupled to CS electrode 134) coupled to terminal 310. As a further alternative, terminals 311, 310, 318 and 320 might all be employed for ventricular defibrillation, with terminals 310, 311 and 320 coupled in common. As yet another alternative, only terminals 310 and 320 might be employed for ventricular defibrillation added or substituted for either of terminals 311 or 318 for treating ventricular fibrillation.

In modern implantable PCD IPGs, the particular therapies are programmed in during a patient work up by the physician, and a menu of therapies is typically provided. For example, on initial detection of an atrial or ventricular tachycardia, an anti-tachycardia pacing therapy may be selected and delivered to the chamber in which the tachycardia is diagnosed or to both chambers. On re-detection of tachycardia, a more aggressive anti-tachycardia pacing therapy may be scheduled. If repeated attempts at anti-tachycardia pacing therapies fail, a higher level cardioversion pulse may be selected thereafter. Therapies for tachycardia termination may also vary with the rate of the detected tachycardia, with the therapies increasing in aggressiveness as the rate of the detected tachycardia increases. For example, fewer attempts at antitachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that atrial or ventricular fibrillation is identified, the typical therapy will be delivery of a high amplitude defibrillation pulse, typically in excess of 10 joules in the case of ventricular fibrillation and about 1 joule or less in the case of atrial defibrillation. Lower energy levels will be employed for cardioversion. As in the case of currently available implantable pacemakers/cardioverter/ defibrillators, and as discussed in the above-cited references, it is envisioned that the amplitude of the defibrillation pulse may be incremented in response to failure of an initial pulse or pulses to terminate fibrillation.

The detection criteria for detection of a tachyarrhythmia and the particular selection of the defibrillation terminals and associated defibrillation electrodes for delivery of the physician prescribed therapies are not of primary importance in the practice of the present invention. The method of the present invention, however, is only practiced when the HV charge circuit 236 is not being operated in response to a detected tachyarrhythmia and when cardioversion/ defibrillation therapies are not being delivered.

Turning to the threshold determination operations of a first embodiment of the invention, the switch matrix 208 is operated in a preferred threshold detection mode for coupling selected pairs of terminals 310, 311,318 and 320 to the input terminals of the atrial sense amplifier 204 or the ventricular sense amplifier 200 during timing windows following the delivery of atrial and ventricular pacing pulses as described below. The switch matrix 208 also uncouples the pace/sense terminals 317, 321 and 324, 326 from the inputs of the atrial and ventricular sense amplifiers 204 and 200, respectively, for the duration of the threshold determination operation. The sense amplifier that is attached to the defibrillation electrodes provides a sense output signal that is processed as described below to distinguish CAPTURE from LOC following delivery of a test pacing pulse.

Turning to the threshold determination operation of a second embodiment of the present invention, the switch matrix 208 can alternatively be employed in a threshold detection mode to preferably couple selected pairs of terminals 310, 311, 318 and 320 to the input terminals of a further sense amplifier. In a first variation of this second embodiment, the wide band EGM amplifier 210 may be switched to the selected terminal pair during a timing window following the delivery of a pacing pulse in the threshold determination operation. The output signal may be then passed through multiplexer 220, digitized in the A/D converter 222 and applied to the microprocessor 224. The digital representation of the signal may then be compared in a pattern recognition or morphology detection manner to a characteristic pulse width capture detect data pattern to determine CAPTURE or LOC in response to a threshold test pace pulse energy.

Figure 6:
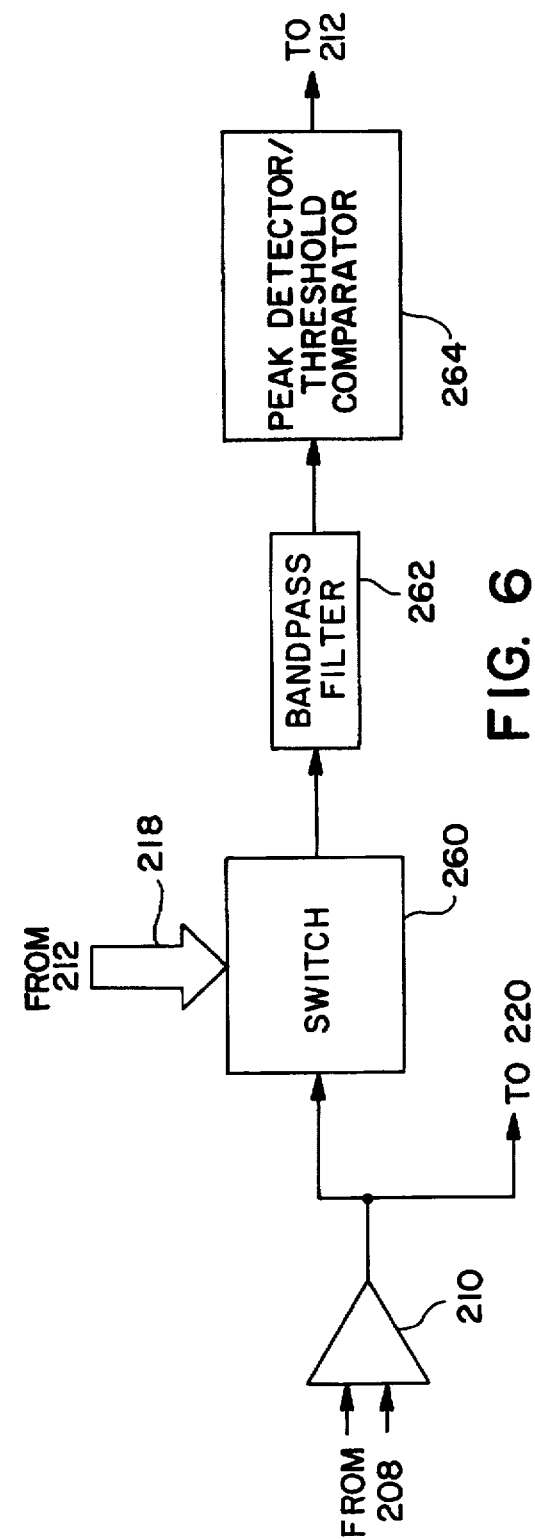
FIG. 6 is a modification of the block diagram of FIG. 2 allowing use of the EGM amplifier in the capmre/LOC threshold determination operation.

In a second variation of this second embodiment, the circuit of FIG. 2 is modified by the addition of components as shown in FIG. 6. The output signal of the EGM amplifier 210 is routed to a bandpass filter 262 through a switch 260 that is closed by a signal on bus 218 from the pacer timing and control circuitry 212 (or the microprocessor 224). The signal is bandpass filtered in a narrower range tailored to the frequency characteristics of the evoked response signal. The filtered, sense output signal is then routed to a peak detector and threshold comparator 264 for peak detection and threshold comparison of the evoked signal in the same manner as the ASENSE and VSENSE signals on the P-OUT and R-OUT lines are processed.

The use of the EGM wide band amplifier 210 for the CAPTURE/LOC function in these two variations of the second embodiment allows the continued, simultaneous processing of the ASENSE and VSENSE signals of the atrial and ventricular sense amplifiers 204 and 200 by the pacer timing and control circuitry. Microprocessor 224 remains capable of detecting the onset of a tachyarrhythmia and of interrupting the threshold determination operation, opening of the switches in the switch matrix 208, and commencement of delivery of an appropriate therapy.

A number of variations of either embodiment are possible to optimize the sensing of the evoked response. Depending on the combination of pacing and defibrillation leads in the particular PCD system and the chamber of the heart subjected to the threshold determination, it may be desirable to couple the selected sense amplifier across a threshold sensing electrode pair comprising a defibrillation electrode and a pace/sense electrode not used to deliver the test pacing pulses rather than across two defibrillation electrodes.

In the first embodiment, and in a dual chamber configuration as depicted in FIG. 2, it may also be desirable to use the atrial sense amplifier 204 for both atrial and ventricular threshold determinations using selected threshold sensing electrode pairs for each chamber. This variation would leave the ventricular sense amplifier 200 enabled to sense ventricular events in case a tachyarryhthmia episode should commence during the threshold test regimen. Because of this possibility, it would not be desirable to use the ventricular sense amplifier 200 in both the atrial and ventricular threshold determination operations.

Combining these two variations, for example, the ventricular threshold test regimen could be conducted by delivering the V-PACE test pulses to the RV pace/sense electrodes 124, 126 while the RV defibrillation electrode 122 and one of the atrial pace/sense electrodes 144 or 146 are coupled to the atrial sense amplifier 204. This may be one option particularly in the case where the system provides dual chamber pacing and/or sensing but only provides ventricular or atrial defibrillation capabilities using only a remote, subcutaneous patch or can electrode 110, and it is desired to use a near-field sensing pathway.

The pacer timing and control circuitry 212 times out a short delay interval T1 followed by a T2 capture detect time window upon delivery of the pacing pulse. The atrial or ventricular evoked response sense output signal is coupled to the pacer timing and control circuitry 212, and if present during a T2 capture detect time window, is classified as a CAPTURE detect that is provided on the address/data bus 218 to RAM in ROM/RAM 226 and is employed in the determination of the stimulation threshold and the setting of the pacing pulse energy level. In the second embodiment described above employing the wide band EGM sense amplifier 210, described above, the wide band EGM sense amplifier 210 output signal is digitized and applied to the microprocessor 224 for where a pulse width measurement may also be undertaken to ensure that an evoked response can be distinguished from fusion beats that can occur when the heart chamber depolarizes spontaneously at about the same time the test pace pulse is delivered. Assuming that such a fusion beat occurs within the T2 capture detect time window described below, it would have a narrower pulse width than an evoked response sense detect pulse. A pulse width threshold comparison is employed to distinguish an evoked response from such a fusion beat.

The threshold determination operation may be conducted in response to programmed in commands or automatically in an auto-capture mode on a periodic basis. In the former case, the resulting data may be telemetered out to the external programmer. In the latter case, stimulation threshold data from a series of auto-capture test stimulation pace events may thereby be stored in RAM in the ROM/RAM 226 associated with microprocessor 224 for later telemetry out on command of the external programmer. This data may also be encoded in digital form and transmitted via an RF transmitter and IPG antenna to the external programmer at a later time for reception, display and/or analysis in a manner well known in the art.

In the normal, everyday operation of the PCD IPG 100, the A-PACE and V-PACE pulse energy in each case may be established initially by programming the pulse widths and amplitudes post-operatively or at a later patient examination. In accordance with the invention, the normal pacing operation is departed from on a periodic schedule or during a programmed-in threshold determination operation to operate pacer timing and control circuitry 212 to provide a threshold test escape interval and to set the A-PACE or V-PACE pulse energies to reduced levels for testing for the capture/LOC stimulation threshold of the atrial or ventricular channel as shown in the timing diagram of FIG. 4. At the same time, for the duration of the threshold determination operation, the switch network 208 is set under commands from microprocessor 224 to couple the appropriate defibrillation electrodes to the appropriate atrial or ventricular sense amplifier 204 or 200 or the EGM amplifier 210.

Figure 5:
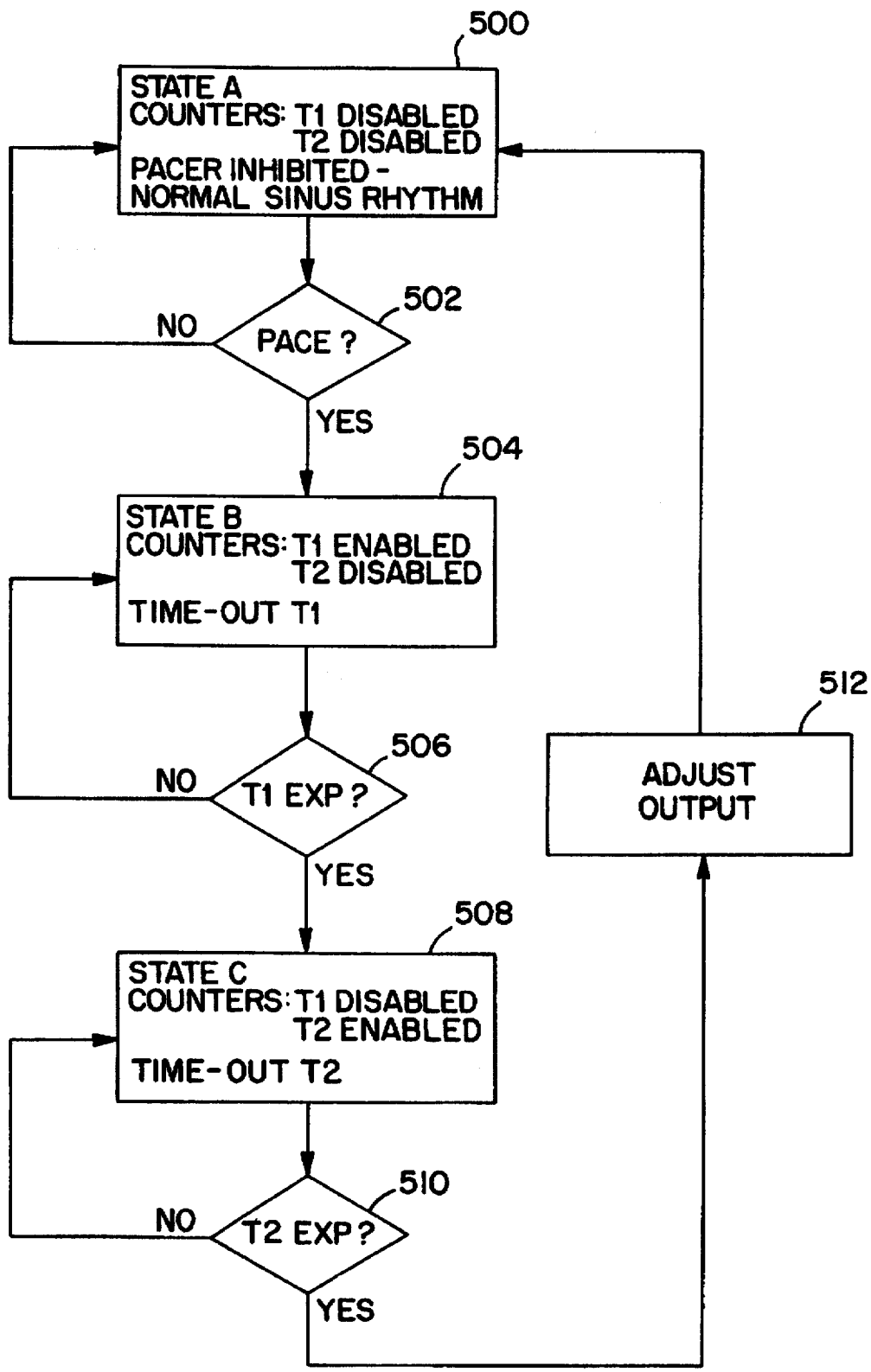
FIG. 5 is a machine description of the process for detecting the evoked response during the timing windows of FIG. 4.

At the delivery of each pacing pulse of the threshold test regimen, timing windows are set in accordance with the state algorithm of FIG. 5 for detecting the evoked response. Both atrial and ventricular stimulation threshold data is derived for storage in memory for telemetry out and analysis and also for use in setting the V-PACE and A-PACE normal pulse width and amplitude used between successive auto-capture tests in order to conserve battery energy. The pacer timing and control circuitry 212, operating in accordance with this aspect of the present invention, is capable of determining the stimulation threshold at atrial loss of capture (ALOC) and ventricular loss of capture (VLOC) in patients having a regular and predictable A-V conduction or first degree A-V block. Of course, as described above, depending on the construction or operating mode of the PCD IPG 100, the threshold determination operation may be conducted with regard to only one channel, and only the ALOC or the VLOC and CAPTURE pulse energy levels may be determined.

Figure 3:
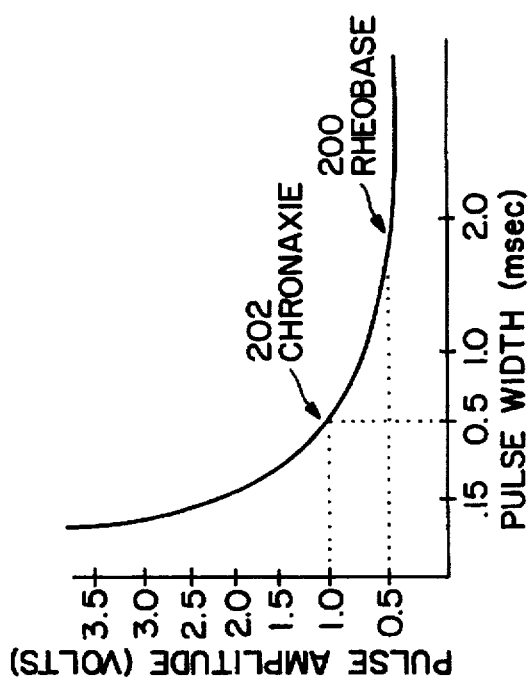
FIG. 3 shows a typical S-D curve for electrical stimulation of myocardial tissue plotted as pulse amplitude in volts versus pulse width in milliseconds.

It should be noted that when the threshold determination operation employs the atrial or ventricular sense amplifier 204 or 200 or the EGM amplifier 210, the switch matrix 208 may be operated to make the connection with the selected threshold sensing electrode pair for the duration of the threshold determination operation. Alternatively, the inputs of the selected sense amplifier 204 or 200 may be switched from their normal pace/sense electrode pair to the selected sensing electrode pair during a test interval including T1 time delay and the T2 capture window and then switched back. To minimize the effects of switching transients, the test interval may begin prior to the T1 time delay. First the S-D characteristics taken into account in the operation of the invention are described in reference to FIG. 3 which shows a typical S-D curve for electrical stimulation of myocardial tissue plotted as pulse amplitude in volts versus pulse width in milliseconds corresponding generally to FIG. 2 of the above-referenced '643 patent. The graph shows, inter alia, that the stimulation threshold increases with a decreasing pulse width, and thus decreases with an increasing pulse width, except that beyond the Rheobase, no further reductions in the amplitude threshold can be achieved. Thus, increasing the pulse width beyond about one millisecond (in the example shown) still requires a threshold of 0.5 volts. Also included on the graph for illustrative purposes is the Chronaxie, a measure of myocardial excitability, which is the point representing the lowest pulse width needed to have an amplitude threshold equal to twice the Rheobase threshold.

It is well known in the art to provide a safety margin between the actual delivered pacing pulse width and amplitude and the stimulation thresholds appearing in the S-D curve. However, as previously stated, the amount of the safety margin may change over time and must be balanced against the need to maximize battery life, as increased amplitude and pulse width will cause a greater battery energy consumption. Physiological changes in the patient may alter the thresholds from the initial programmed value or values, and can lead to loss of capture, with inadequate amplitude or pulse width.

The stored values for both atrial and ventricular pacing pulse width and pulse amplitude will be the actual measured values at CAPTURE or LOC, or both, as determined in the course of conducting the atrial and ventricular pacing threshold tests. The actual stimulation threshold data that are stored and later characterized as Rheobase and Chronaxie may therefore be selected as either the measured value declared as LOC or capture as described below.

It is intended that the threshold determination operation operate automatically only during periods of sleep, and that, if possible, it be initiated about the same time every night by a programmed start time. The stimulation threshold determining algorithm establishes a test pacing rate for the selected heart chamber that is clinically acceptable and not arrhythmogenic but is fast enough to prevent a patient's heart from breaking through with a sinus escape mechanism which thereby causes inhibition of the pacemaker or leads to multiple fusion beat events. In this regard, the pacing rate during the test should not exceed 100 bpm to avoid intolerable patient symptoms from pacing rapidly in patients who may have coronary artery disease or may be sensitive to rapid stimulation. A rate of 60 to 100 bpm is fast enough to prevent intolerable symptoms when a beat is dropped due to LOC. Ventricular rate pauses during the recovery from VLOC described below should be no longer than two seconds.

Turning to FIGS. 4 and 5, they depict a timing diagram which reflects the capture/LOC function timing windows following a delivered pacing pulse by the PCD IPG 100 and a machine description of a procedure for setting time windows and detecting the evoked response during the capture detect timing window for both the atrial and the ventricular channels. The operation of the invention with respect to either the atrial or ventricular chamber is illustrated in FIG. 4 which shows simulated Tracings of pacing pulses, cardiac waveforms and time intervals associated with the threshold determination operation of the present invention. Tracing A depicts an intrinsic depolarization 410 and delivered pacing pulses 412, 414, 416, 418, 420. Tracing F depicts the A-PACE or V-PACE pulses of the atrial or ventricular pacing pulse generators 214 or 216 illustrating the varying pulse energy set by a pace energy control circuit within pacer timing and control circuit 212 during the threshold determination operation illustrated in FIG. 4. The energy of the pacing pulses are reflected by the height of the pulse markers.

Tracing A also depicts the evoked responses 415, 421 in timed relationship to the pacing pulses 414, 420 sufficient in energy to capture the heart chamber as seen at the same near-field pace/sense electrodes that the pacing pulses 414, 420 are delivered across. The illustrated evoked responses 415 and 421 fall within and are masked by the decaying polarization waves (shown in broken lines) elicited on the pace/sense electrodes by the preceding delivered pace pulse 414, 420 and appear at best as minute deflections in the decaying wave that are difficult to detect.

Tracing B depicts the intrinsic signal 400 and the evoked response depolarization signals 402, 404 appearing across the selected defibrillation electrodes corresponding to the signals 410, 415, 421, respectively. Tracing C depicts the sense output signals 422, 424, 426 processed from the atrial or ventricular sense amplifier 204 or 200 corresponding to the signals 400, 402, 404. Tracing D depicts T2 capture detect time windows that are started at the end of the short delay time T1 after delivery of the A-PACE or V-PACE signals 412, 414, 416, 418, 420. Tracing E depicts the atrial or ventricular capture detect signals 438, 440 resulting from the capture determination operation and occurring during the T2 capture detect time windows 430 and 436, respectively. Since the intrinsic depolarization, sense output signal 422 is not within a T2 capture detect time window, it is not detected as a capture detect signal.

Pace pulse 412 on Tracing A and pacing pulse marker 442 on Tracing F indicate the delivery of a first pacing pulse of reduced energy in a threshold detection operation. A T2 capture detect time window 428 is defined thereafter as indicated on Tracing D. No evoked cardiac depolarization results as indicated in tracing B, as the pacing pulse is of insufficient amplitude to capture the heart. A LOC is then declared in the pacer timing and control circuitry 212 from the absence of the capture signal within the T2 capture time window 428. In this instance, the auto-threshold algorithm generates a succeeding pacing pulse 414 at a programmed upper rate limit interval and with an increased energy, as indicated by pacing pulse energy marker 444 in Tracing F.

In this instance, the second pacing pulse 414 captures the heart as evidenced by the signal 402 (Tracing B) across the selected defibrillation electrodes and the sense output signal 424 in Tracing C. This sense output signal 424 is provided to the pacer timing and control circuitry 212 which recognizes its occurrence during the timeout of the capture T2 detection time window 430 and issues the capture detect signal 438 in Tracing E.

The Tracings preceding the depolarization waveform 421 illustrates a sequence of three pacing pulses 416, 418, and 420. The first two pacing pulses of energies 446 and 448 fail to capture the heart, as indicated by the absence of sense detect signals in tracing C. Pacing pulse energy (pulse amplitude and/or width) is increased with each pace pulse, as indicated by pacing pulse markers 446, 448, and 450 (all at the programmable upper rate limit interval). The third pulse 420 is successful in capturing the heart as indicated by sense output signal 426. The LOC and CAPTURE determinations are made in the same manner as described above.

FIG. 5 shows a hardware flow or state diagram setting forth a state machine description of the detection procedure performed by the circuitry of FIG. 2 operating in the manner of FIG. 4. The state diagram of FIG. 5 is applicable to either the atrial or ventricular channel, but the following discussion will be with respect to the ventricular channel, for convenience. The T2 capture detect time window and the preceding T1 time delay are set in state 500. The T1 time delay duration should be short, e.g. about 10-50 milliseconds, for example, and may correspond to or exceed the blanking interval. The T2 capture detection time window duration should be long enough, e.g. about 100-300 ms, for example, to allow a detection of any pacemaker pulse evoked response. In practice, the T1 time delay and T2 capture detection time window durations are preferably programmable. In state A (500) shown in the flow diagram, both the T1 and T2 timing functions of a capture detection timer in pacer timing and control circuit 212 are initially disabled. This state A corresponds to the normal pacing function during sinus rhythm which inhibits the pacing function and when the capture detection and auto-threshold seeking functions are disabled. It will be assumed that the capture detection function is enabled either for periodic auto-threshold determination and associated pacing pulse energy setting or during a programmed-in threshold determination operation.

The occurrence of a V-PACE signal at decision block 502 forces a state transition to state B (504) where the T1 timing function is enabled. As the period T1 times out, the machine moves from state B (504) to state C (508), where the T2 capture detect window is being timed. A sense detect signal occurring during the T2 capture detect window is accepted as the indication of an evoked response and a V-CAPTURE is declared in block 508. The expiration of the T2 capture detect window without a V-CAPTURE being declared, tested at decision block 510, triggers declaration of VLOC, adjustment of the pacing pulse energy at block 512, if necessary, and the return to state A (500).

The microprocessor 224 may be programmed in an auto-capture mode causing the threshold detection operation to be initiated periodically, e.g. every night at a certain time when the patient would be sleeping, to automatically adjust the A-PACE and V-PACE output amplitude and pulse width to test for atrial and ventricular stimulation thresholds. The process followed derives and stores the Rheobase and Chronaxie stimulation threshold values resulting from the tests in RAM in ROM/RAM 226 for later telemetry out and uses the values to automatically reset the normal pacing pulse width and amplitude, reflecting a safety margin, until the next test is conducted. In the process of testing for the thresholds, capture is restored on detection of ALOC and VLOC by applied backup A-PACE or V-PACE pulses at programmed pulse width and amplitude energy.

The automatically adjusted pace pulse parameter (amplitude or pulse width) may be referred to herein as the test stimulus "test value" or "metric", and the other parameter may be referred to herein as the test stimulus "fixed value" or "non-metric". The test value is adjusted throughout the stimulation threshold determination and recovery procedure described below (applicable to either ALOC or VLOC). The fixed value remains constant until the derivation of the LOC threshold values of the test value. The present invention may therefore follow the algorithms described, for example, in the above-incorporated '643 patent.

The illustrated PCD IPG of FIG. 1 and block diagram of FIG. 2 are merely exemplary, and correspond to the general functional organization of most multi-programmable, microprocessor controlled, PCD devices presently commercially available. It is believed that the present invention is most readily practiced in the context of such an IPG architecture, and that the present invention can therefore readily be practiced using the basic hardware of existing microprocessor controlled, single chamber PCD IPGs, or in proposed dual chamber PCD devices of the types listed above. The invention may be implemented primarily by means of variations in the software stored in the ROM/RAM 226, switch matrix 208 and pacer timing and control circuitry 212 for the particular combinations of atrial and/or ventricular sense/ pace and cardioversion/defibrillation functions in the particular PCD device configuration.

However, the present invention may also be usefully practiced in all such configurations by means of a full custom integrated circuit in each case. For example, such a circuit may take the form of a state machine in which a state counter serves to control an arithmetic logic unit to perform calculations according to a prescribed sequence of counter controlled steps.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

I claim:

1. A cardiac pacemaker/defibrillator system operable in a threshold determination operation for determining a stimulation threshold of the heart comprising:

a defibrillation lead system having at least one defibrillation electrode adapted to be positioned in relation to a patient's heart;

a pacing lead system having at least one pace/sense electrode pair adapted to be positioned in relation to a patient's heart;

sense amplifier means adapted to be coupled to said pacing lead system for sensing occurrences of electrical depolarizations of the heart using said pace/sense electrode pair and providing a sense output signal in response thereto indicative of an occurrence of a depolarization;

means responsive to said sense amplifier means for measuring time intervals separating sense output signals;

means responsive to said measuring means for detecting occurrences of tachyarrhythmias based on said measured intervals;

means operable in a threshold determination operation for coupling a threshold sensing electrode pair including at least one defibrillation electrode to said sense amplifier means;

pacing pulse generator means operable in the threshold determination operation for delivering pacing pulses at a stimulation threshold test energy level to the patient's heart through the pacing lead system and at least one pace/sense electrode; and means responsive to a sense output signal of the sense amplifier means for determining capture of the patient's heart by a pacing pulse delivered at the stimulation threshold test energy level.

2. A cardiac pacemaker/defibrillator system comprising:

a defibrillation lead system having at least two defibrillation electrodes adapted to be positioned in relation to a patient's heart;

a pacing lead system having at least two pace/sense electrodes adapted to be positioned in relation to a patient's heart;

sense amplifier means for sensing electrical depolarizations of the heart via said pace/sense electrodes and providing a sense detect signal in response thereto;

pacing pulse generator means coupled to said pace/sense electrodes for providing pacing pulses to the heart in response to a trigger signal;

pacer timing and control means operable in a pacing mode and responsive to said sense detect signals comprising means for timing escape intervals initiated in response to said sense detect signals and means for providing trigger signals to said pacing pulse generator means on expirations of said escape intervals;

defibrillation shock generator means for providing defibrillation shocks across said defibrillation lead system; and defibrillation control means responsive to sense detect signals for controlling the operation of said defibrillation shock generator means;

a system operable in a threshold determination operation for determining capture and loss of capture of the heart in response to test pacing pulse energy level comprising:

means for coupling a threshold sensing electrode pair including at least one defibrillation electrode to the sense amplifier means;

means for causing said pacer timing and control means to provide trigger pulses to said pacing pulse generator means for delivering test pacing pulses at a stimulation threshold test energy levels to the patient's heart through said pace/sense electrodes;

means responsive to sense output signals provided by the sense amplifier means in response to the delivered pacing pulses when the stimulation threshold test energy level is sufficient to capture the heart for indicating capture of the heart; and means responsive to the absence of sense output signals provided by the sense amplifier means in response to the delivered pacing pulses when the stimulation threshold test energy level is insufficient to capture the heart for indicating loss of capture of the heart.

3. The system of claim 2 wherein said threshold sensing electrode pair comprises said defibrillation electrodes.

4. The system of claim 2 wherein:

said coupling means comprises means operable in said threshold determination operation for un-coupling said sense amplifier means from said pace/sense electrodes.

5. The system of claim 2 wherein said sense amplifier means is an EGM sense amplifier.

6. A cardiac pacemaker/defibrillator system operable in a threshold determination operation for determining a stimulation threshold of the heart, comprising:

a defibrillation lead system having at least one defibrillation electrode adapted to be positioned in relation to a patient's heart;

a pacing lead system having at least one pace/sense electrode pair adapted to be positioned in relation to a patient's heart;

sense amplifier means adapted to be coupled to said pacing lead system for sensing occurrences of electrical depolarizations of the heart and providing a sense output signal in response thereto indicative of an occurrence of a depolarization;

means responsive to said sense amplifier means for defining escape intervals following said sense output signals;

means responsive to said defining means for delivering an electrical pulse to said patient's heart in response to an expiration of a said escape interval;

means operable in a threshold determination operation for coupling a threshold sensing electrode pair including at least one defibrillation electrode to said sense amplifier means;

pacing pulse generator means operable in the threshold determination operation for delivering pacing pulses at a stimulation threshold test energy level to the patient's heart through the pacing lead system and at least one pace/sense electrode; and means responsive to a sense output signal of the sense amplifier means for determining capture of the patient's heart by a pacing pulse delivered at the stimulation threshold test energy level.

7. The system of claim 1 or claim 6 further comprising:

means for detecting the absence of a sense output signal from said sense amplifier means following a delivered pacing pulse; and means for determining loss of capture of the patient's heart by a pacing pulse delivered at the stimulation threshold test energy level in response to the detected absence of a sense output signal.

8. The system of claim 1 or claim 6 wherein said threshold sensing electrode pair comprises two defibfillation electrodes.

9. The system of claim 1 or claim 6 wherein said threshold sensing electrode pair comprises one defibfillation electrode and one further electrode.

10. The system of claim 9 wherein said further electrode comprises a further pace/sense electrode.

11. The system of claim 1 or claim 6 wherein:

said coupling means comprises means operable in said threshold determination operation for un-coupling said sense amplifier means from said pace/sense electrodes.

12. The system of claim 1 or claim 6 wherein said sense amplifier means is an EGM sense amplifier.

13. A cardiac pacemaker/cardioverter system, comprising:

a cardioversion lead system having at least one cardioversion electrode adapted to be positioned in relation to a patient's heart;

a pacing lead system having at least one pacing electrode adapted to be positioned in relation to a patient's heart;

first and second sense amplifier means for sensing electrical signals from said patient's heart;

means for generating pacing pulses, coupled to said pacing electrode;

means for detecting occurrences of tachyarrhythmia, coupled to said first amplifier;

control means for defining a first operational mode during which said tachyarrhythmia detecting means is employed to detect occurrences of tachyarrhythmia and a second operational mode during which a threshold determination is made, said control system comprising means for triggering said pacing pulse generating means to deliver pacing pulses during said second mode;

coupling means for coupling said at least one cardioversion lead to said first sense amplifier during said first operational mode and for coupling said at least one cardioversion electrode to said second sense amplifier means during said second operational mode; and capture detection means for detecting capture of said patient's heart during said second operational mode in response to electrical activity sensed by said second sense amplifier means.

14. A pacemaker/cardioverter system according to claim 13, further comprising:

switching means for switching said at least one cardioversion electrode from said first to said second amplifier means.

15. A pacemaker/cardioverter system according to claim 13, wherein said coupling means comprises means for coupling said first amplifier to said at least one cardioversion electrode and means for coupling said first sense amplifier to said second amplifier.

* * * * *